(12) United States Patent
Ironi

(10) Patent No.: US 11,167,135 B2
(45) Date of Patent: Nov. 9, 2021

(54) APPARATUS FOR PROVIDING PAIN RELIEF THERAPY

(71) Applicant: THERANICA BIO-ELECTRONICS LTD., Netanya (IL)

(72) Inventor: Alon Ironi, Haifa (IL)

(73) Assignee: THERANICA BIO-ELECTRONICS LTD., Netanya (IL)

( * ) Notice: Subject to any disclaimer, the term of this patent is extended or adjusted under 35 U.S.C. 154(b) by 134 days.

(21) Appl. No.: 16/614,986

(22) PCT Filed: May 15, 2018

(86) PCT No.: PCT/IB2018/053385
§ 371 (c)(1),
(2) Date: Nov. 19, 2019

(87) PCT Pub. No.: WO2018/215879
PCT Pub. Date: Nov. 29, 2018

(65) Prior Publication Data
US 2020/0206502 A1    Jul. 2, 2020

Related U.S. Application Data

(60) Provisional application No. 62/614,613, filed on Jan. 8, 2018, provisional application No. 62/509,108, filed on May 21, 2017.

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0492* (2013.01); *A61N 1/3603* (2017.08)

(58) Field of Classification Search
CPC .......................... A61N 1/36021; A61N 1/3603
(Continued)

(56) References Cited

U.S. PATENT DOCUMENTS

| 4,613,850 A | 9/1986 | Timmermann |
| 4,785,813 A | 11/1988 | Petrofsky |

(Continued)

FOREIGN PATENT DOCUMENTS

| EP | 2730311 | 5/2014 |
| JP | 2011015723 | 1/2011 |

(Continued)

OTHER PUBLICATIONS

An International Search Report and a Written Opinion both dated Apr. 24, 2017, which issued during the prosecution of Applicant's PCT/IL2017/050028.

(Continued)

*Primary Examiner* — Nadia A Mahmood
(74) *Attorney, Agent, or Firm* — Sughrue Mion, PLLC

(57) ABSTRACT

An apparatus is described comprising electrodes (22) configured to be placed upon a portion of a body of a subject, and a user interface device (26). A computer processor (24) applies a neuromodulation treatment to the subject, by driving electrical pulses into the portion of the subject's body via the electrodes, and generates an output on the user interface device that indicates to the subject a physiological effect that the neuromodulation treatment has upon the subject's body.

20 Claims, 10 Drawing Sheets

(58) Field of Classification Search
USPC .......................................................... 607/46
See application file for complete search history.

(56) References Cited

U.S. PATENT DOCUMENTS

| | | | |
|---|---|---|---|
| 4,811,742 | A | 3/1989 | Hassel et al. |
| 4,989,605 | A | 2/1991 | Rossen |
| 5,330,515 | A | 7/1994 | Rutecki et al. |
| 5,938,690 | A | 8/1999 | Law et al. |
| 5,999,848 | A | 12/1999 | Gord et al. |
| 6,217,574 | B1 | 4/2001 | Webster |
| 6,249,706 | B1 | 6/2001 | Sobota et al. |
| 6,273,863 | B1 | 8/2001 | Avni et al. |
| 6,522,927 | B1 | 2/2003 | Bishay et al. |
| 6,741,889 | B1 | 5/2004 | Holcomb |
| 7,006,859 | B1 | 2/2006 | Osorio et al. |
| 7,155,287 | B2 | 12/2006 | Gavronsky |
| 7,200,444 | B2 | 4/2007 | Gavronsky et al. |
| 7,221,980 | B2 | 5/2007 | Kotlik et al. |
| 7,483,751 | B2 | 1/2009 | Greenberg et al. |
| 7,734,340 | B2 | 6/2010 | De Ridder |
| 7,771,371 | B2 | 8/2010 | Avni |
| 7,998,092 | B2 | 8/2011 | Avni et al. |
| 8,295,925 | B2 | 10/2012 | Brogan et al. |
| 8,306,624 | B2 * | 11/2012 | Gerber ............... A61N 1/37247 607/41 |
| 8,340,771 | B2 | 12/2012 | Thimineur et al. |
| 8,428,734 | B2 | 4/2013 | Rigaux et al. |
| 8,478,420 | B2 | 7/2013 | Armstrong et al. |
| 8,620,434 | B2 | 12/2013 | Bodlaender et al. |
| 8,660,651 | B2 | 2/2014 | Castel et al. |
| 8,712,546 | B2 | 4/2014 | Kim et al. |
| 8,768,428 | B2 | 7/2014 | Clare et al. |
| 8,774,925 | B2 | 7/2014 | Yarnitsky |
| 8,805,548 | B2 | 8/2014 | Mignolet et al. |
| 8,874,205 | B2 | 10/2014 | Simon et al. |
| 8,874,227 | B2 | 10/2014 | Simon et al. |
| 8,880,173 | B2 | 11/2014 | DiUbaldi et al. |
| 8,996,115 | B2 | 3/2015 | Trier et al. |
| 9,011,355 | B2 | 4/2015 | Ehrenreich et al. |
| 9,067,054 | B2 | 6/2015 | Simon et al. |
| 9,138,580 | B2 | 9/2015 | Ignagni et al. |
| 9,205,256 | B2 | 12/2015 | Koo |
| 9,242,085 | B2 | 1/2016 | Hershey et al. |
| 9,242,092 | B2 | 1/2016 | Simon et al. |
| 9,248,279 | B2 | 2/2016 | Chen et al. |
| 9,333,347 | B2 | 5/2016 | Simon et al. |
| 9,375,571 | B2 | 6/2016 | Errico et al. |
| 9,415,219 | B2 | 8/2016 | Simon et al. |
| 9,656,074 | B2 | 5/2017 | Simon et al. |
| 9,895,533 | B2 | 2/2018 | Harpak et al. |
| 10,213,602 | B2 | 2/2019 | Ironi et al. |
| 10,289,594 | B2 | 5/2019 | Harpak et al. |
| 2002/0138116 | A1 | 9/2002 | Bertolucci |
| 2003/0120271 | A1 | 6/2003 | Burnside et al. |
| 2004/0015212 | A1 | 1/2004 | Huber et al. |
| 2004/0030360 | A1 | 2/2004 | Eini et al. |
| 2004/0087838 | A1 | 5/2004 | Galloway et al. |
| 2005/0118497 | A1 | 6/2005 | Breen |
| 2005/0182457 | A1 | 8/2005 | Thrope et al. |
| 2005/0234525 | A1 | 10/2005 | Phillips |
| 2005/0251061 | A1 | 11/2005 | Schuler et al. |
| 2006/0047325 | A1 | 3/2006 | Thimineur et al. |
| 2006/0100671 | A1 | 5/2006 | Ridder |
| 2006/0155345 | A1 | 7/2006 | Williams et al. |
| 2006/0206163 | A1 | 9/2006 | Wahlstrand et al. |
| 2007/0067004 | A1 | 3/2007 | Boveja et al. |
| 2007/0123952 | A1 | 5/2007 | Strother et al. |
| 2007/0203534 | A1 | 8/2007 | Tapper |
| 2007/0233203 | A1 | 10/2007 | Euliano et al. |
| 2008/0021505 | A1 | 1/2008 | Hastings et al. |
| 2008/0033504 | A1 | 2/2008 | Bertolucci |
| 2008/0065182 | A1 | 3/2008 | Strother et al. |
| 2008/0167580 | A1 | 7/2008 | Avni et al. |
| 2008/0215119 | A1 | 9/2008 | Woods et al. |
| 2009/0182393 | A1 | 7/2009 | Bachinski |
| 2009/0192406 | A1 | 7/2009 | Larsen et al. |
| 2010/0137939 | A1 | 6/2010 | Liu |
| 2010/0312166 | A1 | 12/2010 | Castel |
| 2011/0112605 | A1 | 5/2011 | Fahey |
| 2011/0215952 | A1 | 9/2011 | Aria et al. |
| 2011/0245648 | A1 | 10/2011 | Hudson |
| 2011/0264171 | A1 | 10/2011 | Torgerson |
| 2011/0276738 | A1 | 11/2011 | Kim et al. |
| 2012/0083858 | A1 | 4/2012 | Yarnitsky |
| 2012/0116478 | A1 | 5/2012 | Buhlmann et al. |
| 2012/0184801 | A1 | 7/2012 | Simon et al. |
| 2013/0085551 | A1 | 4/2013 | Bachinski et al. |
| 2013/0093501 | A1 | 4/2013 | Kajimoto |
| 2013/0158627 | A1 | 6/2013 | Gozani et al. |
| 2013/0236867 | A1 | 9/2013 | Avni et al. |
| 2013/0245486 | A1 | 9/2013 | Simon et al. |
| 2013/0338729 | A1 | 12/2013 | Spector |
| 2014/0031895 | A1 | 1/2014 | Rahimi et al. |
| 2014/0148870 | A1 | 5/2014 | Burnett |
| 2014/0163645 | A1 | 6/2014 | Dinsmoor et al. |
| 2014/0194946 | A1 | 7/2014 | Thomas et al. |
| 2014/0222102 | A1 | 8/2014 | Lemus et al. |
| 2014/0249601 | A1 | 9/2014 | Bachinski et al. |
| 2014/0296934 | A1 | 10/2014 | Gozani et al. |
| 2014/0324120 | A1 | 10/2014 | Bogie et al. |
| 2014/0364920 | A1 | 12/2014 | Doan et al. |
| 2014/0371814 | A1 | 12/2014 | Spizzirri et al. |
| 2015/0005852 | A1 | 1/2015 | Hershey et al. |
| 2015/0148878 | A1 | 5/2015 | Yoo et al. |
| 2015/0165186 | A1 | 6/2015 | Dar et al. |
| 2015/0174406 | A1 | 6/2015 | Lamensdorf et al. |
| 2015/0257970 | A1 | 9/2015 | Mucke et al. |
| 2015/0352357 | A1 | 12/2015 | Wei et al. |
| 2017/0001003 | A1 | 1/2017 | Pivonka et al. |
| 2017/0197077 | A1 | 7/2017 | Harpak et al. |
| 2017/0368344 | A1 | 12/2017 | Ironi et al. |
| 2018/0189212 | A1 | 7/2018 | Harpak et al. |

FOREIGN PATENT DOCUMENTS

| | | | |
|---|---|---|---|
| KR | 20110120810 | 11/2011 | |
| WO | 01/36051 | 5/2001 | |
| WO | 2005/039693 | 5/2005 | |
| WO | 2006/029257 | 3/2006 | |
| WO | 2008/128215 | 10/2008 | |
| WO | 2009/079270 | 6/2009 | |
| WO | 2010/143164 | 12/2010 | |
| WO | 2011/053607 | 5/2011 | |
| WO | 2013/134330 | 9/2013 | |
| WO | 2015/042365 | 3/2015 | |
| WO | 2016/025323 | 2/2016 | |
| WO | 2016113661 | 7/2016 | |
| WO | 2016/125087 | 8/2016 | |
| WO | 2016/135604 | 9/2016 | |
| WO | 2016/203356 | 12/2016 | |
| WO | 2017/051412 | 3/2017 | |
| WO | WO-2017051412 | * 3/2017 | ......... A61N 1/36103 607/46 |
| WO | 2017/122195 | 7/2017 | |
| WO | 2018/060997 | 4/2018 | |

OTHER PUBLICATIONS

An International Search Report and a Written Opinion both dated Dec. 14, 2016, which issued during the prosecution of Applicant's PCT/IL2016/051043.

Degen et al., "An improved Method to continuously monitor the Electrode-Skin Impedance during Bioelectric Measurements", Proceedings of the 29th Annual International Conference of the IEEE EMBS Cite Internationale, Lyon, France, pp. 6294-6297, Aug. 23-26, 2007.

An International Search Report and a Written Opinion both dated Apr. 20, 2016, which issued during the prosecution of Applicant's PCT/IB2016/050104.

An Office Action dated Apr. 4, 2018, which issued during the prosecution of U.S. Appl. No. 15/542,553.

(56) References Cited

OTHER PUBLICATIONS

An Office Action dated Mar. 6, 2017, which issued during the prosecution of U.S. Appl. No. 14/992,046.
Notice of Allowance dated Sep. 24, 2018, which issued during the prosecution of U.S. Appl. No. 15/542,553.
Notice of Allowance dated Oct. 27, 2017, which issued during the prosecution of U.S. Appl. No. 14/992,046.
Slavin, Konstantin V., Hrachya Nersesyan, and Christian Wess. "Peripheral neurostimulation for treatment of intractable occipital neuralgia." Neurosurgery 58.1 (2006): 1 12-119.
Ristic, Dejan, and Jens Eilrich. "Innocuous peripheral nerve stimulation shifts stimulus-response function of painful laser stimulation in man." Neuromodulation: Technology at the Neural Interface 17.7 (2014): 686-695.
Nir, Rony-Reuven, et al. "A psychophysical study of endogenous analgesia: the role of the conditioning pain in the induction and magnitude of conditioned pain modulation." European Journal of Pain 15.5 (2011): 491-497.
Burstein, Rami, Michael F. Cutrer, and David Yarnitsky. "The development of cutaneous allodynia during a migraine attack clinical evidence for the sequential recruitment of spinal and supraspinal nociceptive neurons in migraine." Brain 123.8 (2000): 1703-1709.
Johnson MI. Transcutaneous electrical nerve stimulation (TENS) and TENS-like devices: Do they provide pain relief? Journal of Pain 2001;8:121-58.
Melzack R. Prolonged relief of pain by brief, intense transcutaneosomatic stimulation. Journal of Pain. 1975;1:357-73.
Bowman BR, Baker LL. Effects of waveform parameters on comfort during transcutaneous neuromuscular electrical stimulation. Annals of Biomedical Engineering. 1985;13:59-74.
Walsh DM, Foster NE, Baxter GD, Allen JM. Transcutaneous electrical nerve stimulation. relevance of stimulation parameters to neurophysiological and hypoalgesic effects. American Journal of Physical Medicine and Rehabilitation. 1995;74: 199-206.
Petrofsky JS, Suh HJ, Gunda S, Prowse M, Batt J. Interrelationships between body fat and skin blood flow and the current required for electrical stimulation of human muscle. Medical Engineering & Physics. 2008;30: 931-6.
Gopalkrishnan P, Sluka KA. Effect of varying frequency, intensity, and pulse duration of transcutaneous electrical nerve stimulation on primary hyperalgesia in inflamed rats. Archives of Physical Medicine and Rehabilitation. 2000;81: 984-90.
Han JS, Chen XH, Sun SL, Xu XJ, Yuan Y, Yan SC, Hao JX, Terenius L. Effect of low- and high-frequency TENS on Met-enkephalin-Arg-Phe and dynorphin A immunoreactivity in human lumbar CSF. Journal of Pain, vol. 47, Issue 3, Dec. 1991, pp. 295-298.
Melzack R, Wall PD; Pain mechanisms: a new theory; Science. 1965; 150(3699):971-979.
Tong KC, Lo SK, Cheing GL; Alternating frequencies of transcutaneous electric nerve stimulation: does it produce greater analgesic effects on mechanical and thermal pain thresholds; Archives of Physical Medicine and Rehabilitation, Oct. 2007;88(10): 1344-9.
Chen CC, Johnson MI; An investigation into the effects of frequency-modulated transcutaneous electrical nerve stimulation (TENS) on experimentally-induced pressure pain in healthy human participants; Journal of Pain, Oct. 2009;10(10):1029-37.
Yarnitsky D., Conditioned pain modulation (the diffuse noxious inhibitory control-like effect): its relevance for acute and chronic pain states; Current Opinion on Anaesthesiology, Oct. 2010;23(5):611-5.
Youssef A.M., V.G. Macefield V.G., Henderson L.A.; Pain inhibits pain; human brainstem mechanisms; NeuroImage 124 (2016) 54-62.
Marina De Tommaso, Olimpia Difruscolo, Michele Sardaro, Giuseppe Libro, Carla Pecoraro, Claudia Serpino, Paolo Lamberti, Paolo Livrea; Effects of remote cutaneous pain on trigeminal laser-evoked potentials in migraine patients; Journal of Headache Pain (2007) 8:167-174.
Ossipov M.H., Morimura K., Porreca F.; Descending pain modulation and chronification of pain; Current Opinion in Supportive & Palliative Care: Jun. 2014—vol. 8—Issue 2—p. 143-151.
U.S. Appl. No. 62/102,606, filed Jan. 13, 2015.
Notice of Allowance dated Nov. 26, 2018, which issued during the prosecution of U.S. Appl. No. 15/542,553.
Supplementary European Search Report dated Sep. 18, 2018, which issued during the prosecution of Applicant's European App No. 16737139.2.
Notice of Allowance dated Feb. 6, 2019, which issued during the prosecution of U.S. Appl. No. 15/736,181.
L9780 datasheet—Wide range air fuel sensor control interface. DocID026356 Rev Nov. 3, 2014. (Retrieved from the internet on Sep. 1, 2016) Retrieved from the Internet: <http://www.st.com/content/ccc/resource/technical/document/datasheet/42/c9/eb/7c/85/b9/48/fl/DM00116669.pdf/files/DM00116669.pdf/jcr:content/translations/en.DMOO 116669.pdf>STMicroelectronics NV. Nov. 30, 2014.
Communication buses and protocols for sensor networks. Sensors, 2(7), pp. 244-257. (Retrieved from the internet on Sep. 1, 2016) Retrieved from the Internet: <http://www.mdpi.net/sensors/papers/s20700244 ,pdf> Zhou, J. and Mason, A.,Dec. 31, 2002.
An International Search Report and a Written Opinion both dated Sep. 1, 2016, which issued during the prosecution of Applicant's PCT/IB2016/053463.
U.S. Appl. No. 62/180,077, filed Jun. 16, 2015.
Perttunen J, "Foot Loading in Normal and Pathological Walking," Jyväskylä: University of Jyväskylä, 2002, 86 p. (Studies in Sport, Physical Education and Health).
U.S. Appl. No. 62/221,146, filed Sep. 21, 2015.
An Invitation to pay additional fees dated Jul. 30, 2018, which issued during the prosecution of Applicant's PCT/IB2018/053385.
An International Search Report and a Written Opinion both dated Sep. 25, 2018, which issued during the prosecution of Applicant's PCT/IB2018/053385.
An International Search Report and a Written Opinion both dated Dec. 19, 2017, which issued during the prosecution of Applicant's PCT/IL2017/051087.
An Office Action dated Oct. 18, 2018, which issued during the prosecution of U.S. Appl. No. 15/736,181.
An International Search Report and a Written Opinion both dated Aug. 27, 2019, which issued during the prosecution of Applicant's PCTIL2019050045.
An Office Action dated May 1, 2020, which issued during the prosecution of U.S. Appl. No. 15/761,614.
Electroacupuncture reduces Back Pain in Elderly Patients. Acupuncture Today, Aug. 2003 vol. 04, Iss 08._(Retrieved from the internet on Dec. 11, 2016) Retrieved from the Internet: <https://www.acupuncturetoday.com/pdf_out/AcupunctureToday.com-Electroacupuncture-Reduces-Back-Pain-in-Elderly-Patients-1576058026.pdf>.
U.S. Appl. No. 61/186,027, filed Jun. 11, 2009.
Granot, Michal, et al. "Determinants of endogenous analgesia magnitude in a diffuse noxious inhibitory control (DNIC) paradigm: do conditioning stimulus painfulness, gender and personality variables matter?" Pain 136.1-2 (2008): 142-149.—an Abstract.
U.S. Appl. No. 62/401,380, filed Sep. 29, 2016.
U.S. Appl. No. 62/401,392, filed Sep. 29, 2016.
U.S. Appl. No. 62/412,981, filed Oct. 26, 2016.
An Office Action dated Dec. 29, 2019, which issued during the prosecution of Japanese Patent Application No. 2017-554658.
U.S. Appl. No. 62/509,108, filed May 21, 2017.
U.S. Appl. No. 62/614,613, filed Jan. 8, 2018.
Final Office Action issued in U.S. Appl. No. 15/761,614, dated Aug. 25, 2020.
Stovner LJ, Nichols E, Steiner TJ, et al., "Global, regional, and national burden of migraine and tension-type headache", 1990-2016: a systematic analysis for the Global Burden of Disease Study 2016. The Lancet Neurology 2018; 17: 954-976.
Singer AB, Buse DC, Seng EK, "Behavioral Treatments for Migraine Management: Useful at Each Step of Migraine Care", Curr Neurol Neurosci Rep 2015; 15: 14. (8 pages total).

(56) References Cited

OTHER PUBLICATIONS

Pistoia F, Sacco S, Carolei A, "Behavioral Therapy for Chronic Migraine", Curr Pain Headache Rep 2013; 17: 304. (8 pages total).

Yarnitsky D, Volokh L, Irani A, et al., "Nonpainful remote electrical stimulation alleviates episodic migraine pain", Neurology 2017; 88: 1250-1255.

Yarnitsky D, Dodick DW, Grosberg BM, et al., "Remote Electrical Neuromodulation (REN) Relieves Acute Migraine: A Randomized, Double-Blind, Placebo-Controlled, Multicenter Trial", Headache: The Journal of Head and Face Pain 2019; 59: 1240-1252.

Rapoport AM, Bonner JH, Lin T, et al., "Remote electrical neuromodulation (REN) in the acute treatment of migraine: a comparison with usual care and acute migraine medications", The journal of headache and pain 2019; 20: 83. (7 pages total).

Marmura MJ, Lin T, Harris D, et al., "Incorporating Remote Electrical Neuromodulation (REN) Into Usual Care Reduces Acute Migraine Medication Use: An Open-Label Extension Study", Front Neurol; 11. Epub ahead of print 2020. DOI: 10.3389/fneur.2020.00226. (8 pages total).

\* cited by examiner

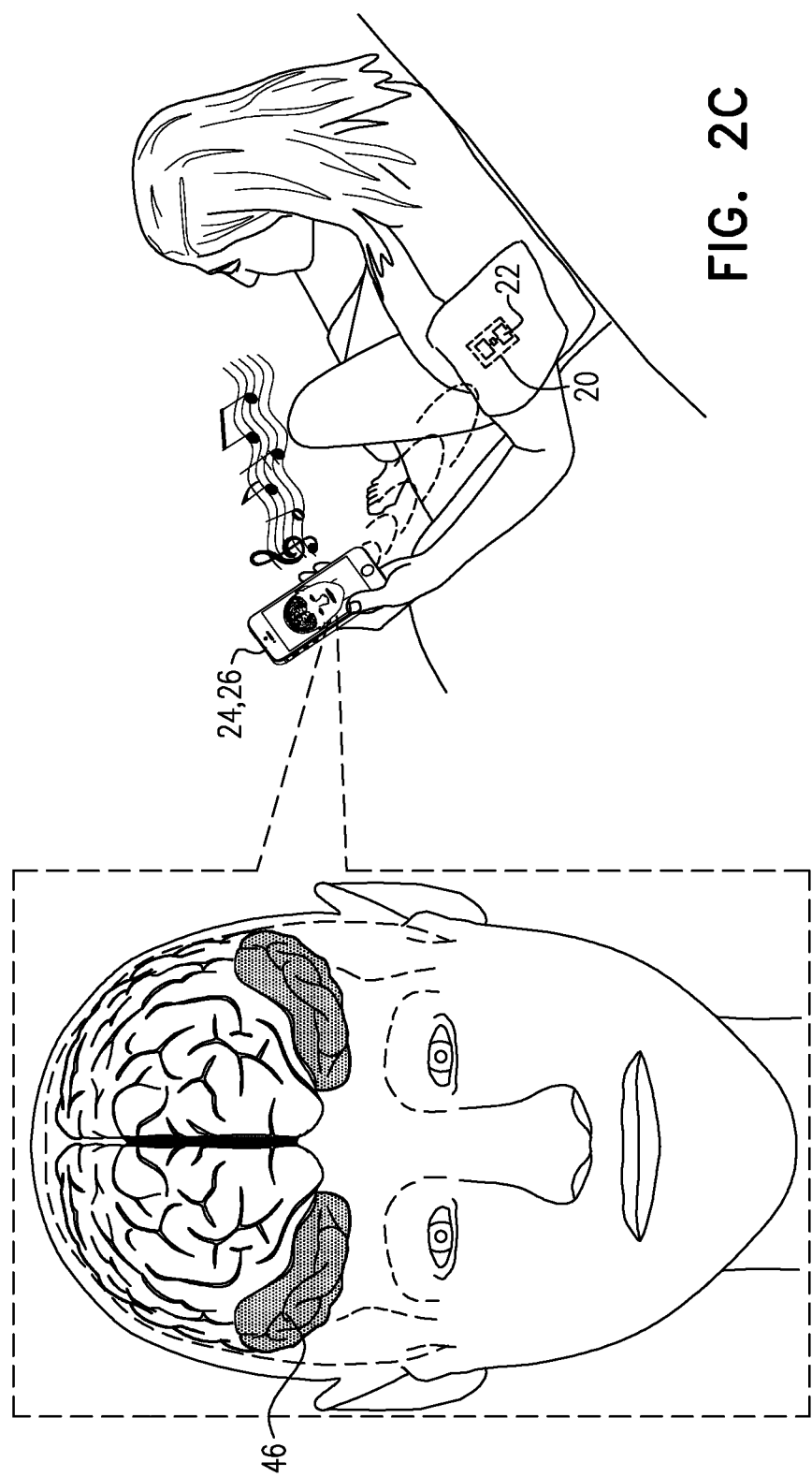

APPARATUS FOR PROVIDING PAIN RELIEF THERAPY

CROSS-REFERENCE TO RELATED APPLICATIONS

The present application is the U.S. national stage of International Application PCT/IB2018/053385, filed May 15, 2018, which claims priority from:

U.S. Provisional Patent Application 62/509,108 to Ironi, filed May 21, 2017, entitled "Pain relief therapy by combining neuromodulation and relaxation;" and U.S. Provisional Patent Application 62/614,613 to Ironi, filed Jan. 8, 2018, entitled "Guided electrical stimulation."

The above-referenced applications are incorporated herein by reference.

FIELD OF EMBODIMENTS OF THE INVENTION

Some applications of the present invention generally relate to medical apparatus and methods. Specifically, some applications of the present invention relate to apparatus and methods for treatment of pain, neurostimulation, and psychological therapy.

BACKGROUND

Migraine is a common neurovascular disorder manifesting itself in attacks of headaches that can reach a level of severe pain in many patients, leading to substantial functional impairment. To date, the pathophysiology of migraine is not fully understood. The current approach to migraine treatment is predominantly pharmacological.

Electrical nerve stimulation has been used as a possible treatment for acute pain relief, including headaches. Clinical studies have shown that two ranges of pulse frequencies (high frequency and low frequency) are especially effective for pain relief.

Conditioned pain modulation is a paradigm used in pain research, in which a "conditioning stimulus" (also referred to as a "secondary stimulus) is applied such as to influence the body's response to a test stimulus, namely a second painful stimulus, referred to as "conditioned stimulus," or "primary stimulus," delivered at a different body location. Painful stimuli have been shown to be inhibited using conditioned pain modulation. The source of the inhibitory process is thought to be a descending, endogenous analgesic mechanism originating in the brainstem.

In last two decades, there has been a lot of research into developing and clinically validating psychological therapies for treating pain. The drive for this research is the growing understanding that pain is a complex interpretation, that is performed within the central nervous system (CNS), of multiple sensations provided by the peripheral nervous system (PNS).

Some such therapies take relaxation-based approaches, the aim of such approaches being to reduce sympathetic arousal and to create a state of bodily relaxation. This approach is based upon the assumption that a reduced sympathetic arousal, together with the modulation of attention through distraction, may help to reduce the central processing of peripheral sensory inputs. This was demonstrated by Andrasik ("Behavioral treatment of migraine: current status and future directions," Expert Rev. Neurother. 2004; 4:403-13.)

It has been shown that educational interventions can improve awareness and self-efficacy for pain control. It has also been shown that guided imagery may be effective in reducing the sensation of pain, and reducing physical limitations caused by pain.

SUMMARY OF EMBODIMENTS

For some applications, the apparatus and methods described herein are used to treat a migraine, a headache, fibromyalgia, dysmenorrhea, post-traumatic headache, and/or another form of pain. Typically, a pain-relief neuromodulation treatment is applied to the subject, by driving electrical pulses into a portion of the subject's body. For some applications, relaxation techniques are used to contain feelings of anxiety, which commonly contribute to the development of migraine, and/or other forms of pain (e.g., forms of pain described hereinabove). For example, such relaxation techniques include progressive muscle relaxation training, diaphragmatic breathing, autogenic training, guided imagery, and/or meditation.

For some applications, an output is generated that indicates to the subject a physiological effect that the pain-relief neuromodulation treatment has upon the subject's body. Typically, the output that is generated is synchronized with stages of the neuromodulation treatment, such that the output that is generated at a given time corresponds with the current stage of the neuromodulation treatment and the corresponding physiological effect on the subject's body. Further typically, generating the output reinforces the effectiveness of the neuromodulation treatment, for example, by educating the subject as to the effects of the neuromodulation treatment, and/or by aiding the subject to feel the physiological effects that the neuromodulation treatment is having.

Typically, the output is generated by a computer processor upon a user interface device, which may include a smartphone, a tablet device, and/or a personal computer. In accordance with respective applications, the output may include an audio output, a graphical output, and/or a combined audio and graphical output (e.g., an output in movie format). For some applications, the output includes an indication of an afferent signal propagating from the portion of the subject's body at which the electrical pulses are applied toward the central nervous system (e.g., toward the brain). For example, the output may include a graphical representation of afferent neurotransmitters travelling from the portion of the subject's body at which the electrical pulses are applied toward the central nervous system. Alternatively or additionally, the output includes an indication of an efferent signal propagating from the central nervous system (e.g., from the brain) to a location at which the subject is feeling pain. For example, the output may include a graphical representation of efferent neurotransmitters travelling from the central nervous system (e.g., from the brain) to a location at which the subject is feeling pain. For some applications, respective categories of neurotransmitters are represented by respective, different graphical representations, e.g., as described in further detail hereinbelow.

For some applications, the computer processor initially generates an output indicative of a region at which the subject feels pain prior to the neuromodulation treatment commencing. For example, if the subject is suffering from a migraine, the computer processor may drive the user interface to display an image of a head with a glow within the head at a region at which the subject is feeling the migraine. For some applications, the indication of the region at which the subject is experiencing pain is generated interactively, by receiving inputs from the subject that are indicative of the type and/or location of pain that the subject is experiencing. Typically, over the duration of the neuromodulation treatment, the computer processor generates an output indicating that the size of the region and/or the level of pain is decreasing.

For some applications, the computer processor is additionally configured to generate an output (e.g., an audio output, a graphical output, and/or a combination thereof) that is configured to guide the subject through a guided relaxation procedure, and/or through a guided breathing procedure.

For some applications, a pain-relief neuromodulation treatment is applied that is generally in accordance with techniques described in US 2017/0368344 to Ironi and/or in WO 18/060997 to Ironi, both of the aforementioned applications being incorporated herein by reference. For some applications, in response to the subject experiencing pain in a first anatomical region, electrodes are placed on a second anatomical region of the subject body (which is a different from the first anatomical region). The neuromodulation treatment is applied by driving electrical pulses into the second anatomical region, via the electrodes. For some applications, the electrodes are placed at location that is at a distance of more than 25 cm from the location at which the subject is experiencing pain, and the electrical pulses are applied the location at which the electrodes are placed. Typically, by applying electrical pulses at the second anatomical region, pain at the first anatomical region is reduced via the conditioned pain modulation mechanism.

As described hereinabove, for some applications, relaxation techniques are used to contain feelings of anxiety, which commonly contribute to the development of migraine, and/or other forms of pain (e.g., as described hereinabove). For some applications, a subject is guided to relax his/her muscles by providing a muscle-relaxation neuromodulation treatment, in combination with muscle-relaxation guidance. For example, an output may be generated such as to guide the subject to contract a muscle during a first time period, and to release tension in the muscle during a second time period, the first and second periods being applied in an alternating cycle. At the same time, an electrical stimulation signal may be applied to a portion of the subject's body that is configured to contract a muscle of the subject during the first time period (by the signal being applied with a first set of parameters), and to release tension in the muscle during the second time period (by the signal being applied with a first set of parameters). In this manner, the guidance and the electrical stimulation typically have a synergistic effect, and enhance muscle relaxation. For example, the electrical stimulation signal may be applied at a first pulse width during the first period, and at a second pulse width during the second period, in synchronization with the generated output, such that, due to the electrical stimulation (a) in transitions from the second period to the first period, the subject senses a contraction sensation, and (b) in transitions from the first period to the second period, the subject senses a tension-release sensation.

There is therefore provided, in accordance with some applications of the present invention, apparatus including:

electrodes configured to be placed upon a portion of a body of a subject;

a user interface device; and at least one computer processor configured to:

apply a neuromodulation treatment to the subject, by driving electrical pulses into the portion of the subject's body via the electrodes; and generate an output on the user interface device that indicates to the subject a physiological effect that the neuromodulation treatment has upon the subject's body.

In some applications, the computer processor is configured to reduce pain in a location of the subject's body that is at a distance of more than 25 cm from the portion of the subject's body into which the electrical pulses are driven, by driving the electrical pulses into the portion of the subject's body.

In some applications, the at least one computer processor is configured to reinforce an effectiveness of the neuromodulation treatment, by generating the output.

In some applications, the at least one computer processor is configured to generate the output by generating an audio output.

In some applications, the at least one computer processor is configured to generate the output by generating a combined audio and graphical output.

In some applications, the at least one computer processor is configured to generate the output by generating an output that is indicative of an afferent signal propagating from the portion of the subject's body toward a central nervous system of the subject.

In some applications, the at least one computer processor is configured to generate the output by generating an output that is indicative of an efferent signal propagating from a central nervous system of the subject to a location at which a subject is feeling pain.

In some applications, the at least one computer processor is configured to generate the output by generating an output that is indicative of a region at which the subject feels pain prior to the neuromodulation treatment commencing, and indicating that a size of the region decreases over a duration of the neuromodulation treatment.

In some applications, the at least one computer processor is further configured to generate an output that is configured to guide the subject through a guided relaxation procedure.

In some applications, the at least one computer processor is further configured to generate an output that is configured to guide the subject through a guided breathing procedure.

In some applications, the at least one computer processor is configured to generate the output by generating a graphical output in which respective categories of neurotransmitters are represented by respective, different graphical representations.

There is further provided, in accordance with some applications of the present invention, a method including:

applying a neuromodulation treatment to a subject, by driving electrical pulses into a portion of a body of the subject; and generating an output that indicates to the subject a physiological effect that the neuromodulation treatment has upon the subject's body.

There is further provided, in accordance with some applications of the present invention, apparatus including:

one or more electrodes configured to be placed on a portion of a subject's body;

a user-interface device; and at least one computer processor configured to:

drive the user-interface device to generate an output such as to guide the subject to contract a muscle during a first time period, and to release tension in the muscle during a second time period, the first and second periods being applied in an alternating cycle; and drive an electrical stimulation signal into the portion of the subject's body via the electrodes, the electrical stimulation signal being applied using a first set of parameters during the first period, and using a second set of parameters during the second period, in synchronization with the generated output, such that, due to the electrical stimulation:

in transitions from the second period to the first period, the subject senses a contraction sensation, and in transitions from the first period to the second period, the subject senses a tension-release sensation.

In some applications, the computer processor is configured to drive the user-interface device to generate the output by driving the user-interface device to generate an output such as to guide the subject to contract the muscle during the first time period, and to release tension in the muscle during the second time period, a ratio of the first time period to the second time period being between 2:3 and 1:3.

In some applications, the computer processor is configured to reduce pain in a location of the subject's body that is at a distance of more than 25 cm from the portion of the subject's body to which the electrical stimulation is applied, by driving the electrical stimulation signal into the portion of the subject's body via the electrodes.

In some applications, the computer processor is configured to drive the electrical stimulation signal into the portion of the subject's body via the electrodes using a first pulse width during the first period, and using a second pulse width during the second period, the first and second pulse widths being different from each other.

In some applications, the computer processor is configured to drive the electrical stimulation signal into the portion of the subject's body via the electrodes using a pulse width of between 160 microseconds and 240 microseconds during the first period, and using a pulse width of between 60 microseconds and 140 microseconds during the second period.

In some applications, the computer processor is configured to drive the electrical stimulation signal into the portion of the subject's body via the electrodes using a pulse width of between 180 microseconds and 220 microseconds during the first period, and using a pulse width of between 80 microseconds and 120 microseconds during the second period.

There is further provided, in accordance with some applications of the present invention, a method including:

identifying a subject as suffering from a medical condition selected from the group consisting of: a migraine, a headache, fibromyalgia, dysmenorrhea, post-traumatic headache, and pain; and in response thereto:

generating an output such as to guide the subject to contract a muscle during a first time period, and to release tension in the muscle during a second time period, the first and second periods being applied in an alternating cycle; and applying electrical stimulation signal to a portion of a body of the subject, the electrical stimulation signal being applied using a first set of parameters during the first period, and using a second set of parameters during the second period, in synchronization with the generated output, such that, due to the electrical stimulation:

in transitions from the second period to the first period, the subject senses a contraction sensation, and in transitions from the first period to the second period, the subject senses a tension-release sensation.

The present invention will be more fully understood from the following detailed description of embodiments thereof, taken together with the drawings, in which:

BRIEF DESCRIPTION OF THE DRAWINGS

FIGS. 2A, 2B, and 2C are schematic illustrations of examples of outputs that are generated to correspond with the current stage of a neuromodulation treatment and the corresponding physiological effect on the subject's body, in accordance with some applications of the present invention;

DESCRIPTION OF EMBODIMENTS

Figure 1:
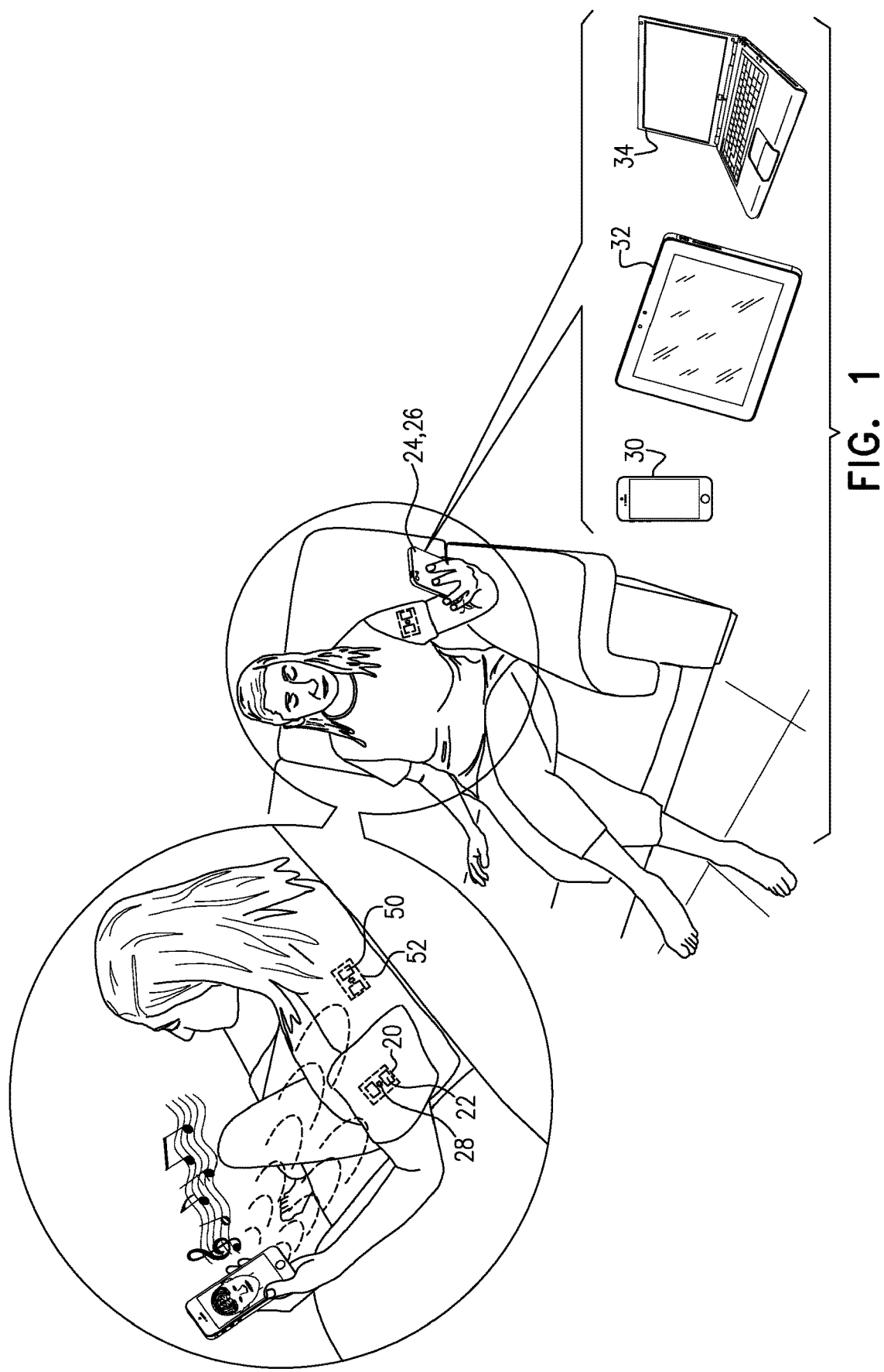
FIG. 1 is a schematic illustration of a patch having electrodes disposed thereon, a computer processor, and a user interface, in accordance with some applications of the present invention.

Reference is now made to FIG. 1, which is a schematic illustration of a patch 20 that supports electrodes 22 disposed on a subject's arm, a computer processor 24, and a user interface 26, in accordance with some applications of the present invention. For some applications, the apparatus and methods described herein are used to treat a migraine, a headache, fibromyalgia, dysmenorrhea, post-traumatic headache, and/or another form of pain.

For some applications, a pain-relief neuromodulation treatment is applied that is generally in accordance with techniques described in US 2017/0368344 to Ironi and/or in WO 18/060997 to Ironi, both of the aforementioned applications being incorporated herein by reference. For some applications, in response to the subject experiencing pain in a first anatomical region, the electrodes are placed on a second anatomical region of the subject body (which is a different from the first anatomical region). A pain-relief neuromodulation treatment is applied by driving electrical pulses into the second anatomical region. For some applications, the electrodes are placed at location that is at a distance of more than 25 cm from the location at which the subject is experiencing pain, and the electrical pulses are driven into the subject's body at the location at which the electrodes are placed. Typically, by applying electrical pulses at the second anatomical region, pain at the first anatomical region is reduced via the conditioned pain modulation mechanism.

For some applications, transcutaneous electrical energy is applied using electrodes 22 disposed on patch 20. For some applications, upon experiencing a migraine or a headache, the subject places patch 20 upon a part of the subject's body, such as the subject's upper arm, as shown in FIG. 1. For some applications, rather than placing a patch on the subject, the subject wears a cuff, sleeve, or wrap having a plurality of electrodes 22 coupled thereto. For some applications, the electrodes are placed on a different portion of the subject's body, such as a different location on the subject's arm, on the subject's hands, legs, feet, and/or lower abdomen (e.g., in order to treat the subject for dysmenorrhea). Typically, the electrodes are placed in electrical contact with the subject's skin. Further typically, an electronics module 28 contained within the patch controls the electrodes, in response to control signals, which are typically wirelessly received from the computer processor.

For some applications, user interface 26 includes user interface components of one or more devices, such as a smartphone 30, a tablet device 32, and/or a personal computer 34. Typically, for such applications, computer processor 24 is the computer processor of the device. It is noted that although FIG. 1 shows the user using a smartphone as the user interface and the computer processor, the scope of the present application includes using other devices for this purpose, e.g., tablet device 32, or personal computer 34. For some applications, electronics module 28 performs some of the computer processor functionalities that are described herein. Alternatively or additionally, the electronics module is used to facilitate communication between a computer processor of an external device (such as smartphone 30, tablet device 32, and/or personal computer 34) and the electrodes, typically using known protocols, such as Wifi, Bluetooth®, ZigBee®, or any near field communication (NFC) protocol.

Electronics module 28 typically comprises a power source, a central processing unit (CPU), typically programmed in microcode, that controls the electrodes, one or more memory units for storing the stimulation sequences during the stimulation, an impulse generator, and components for wireless communication. For some applications, the electronics module is an integrated system-on-chip (SoC).

For some applications, the computer processor receives an input from the subject that indicates that the subject is experiencing a headache, a migraine, fibromyalgia, dysmenorrhea, post-traumatic headache, and/or another form of pain, via a program or application that is run on the computer processor (e.g., a program or application that is run on smartphone 30, tablet device 32, and/or personal computer 34). In response to the input, the computer processor communicates a control signal to the electronics module. Typically, in response to receiving the control signal, the electronics module drives the electrodes to initiate a neuromodulation treatment by driving electrical pulses into the subject (e.g., into the subject's upper arm, as shown in FIG. 1). For some applications, the computer processor receives an input from the subject indicating a particular treatment program, and/or control stimulation parameters (such as the intensity of the stimulation) that should be provided.

For some applications, the computer processor is configured to generate an output that indicates to the subject a physiological effect that the neuromodulation treatment has upon the subject's body. Typically, the output is synchronized with stages of the neuromodulation treatment, such that the output that is generated at a given time corresponds with the current stage of the neuromodulation treatment and the corresponding physiological effect on the subject's body. Further typically, generating the output reinforces the effectiveness of the neuromodulation treatment, for example, by educating the subject as to the effects of the neuromodulation treatment, and/or by aiding the subject to feel the physiological effects that the neuromodulation treatment is having.

Figure 2A:
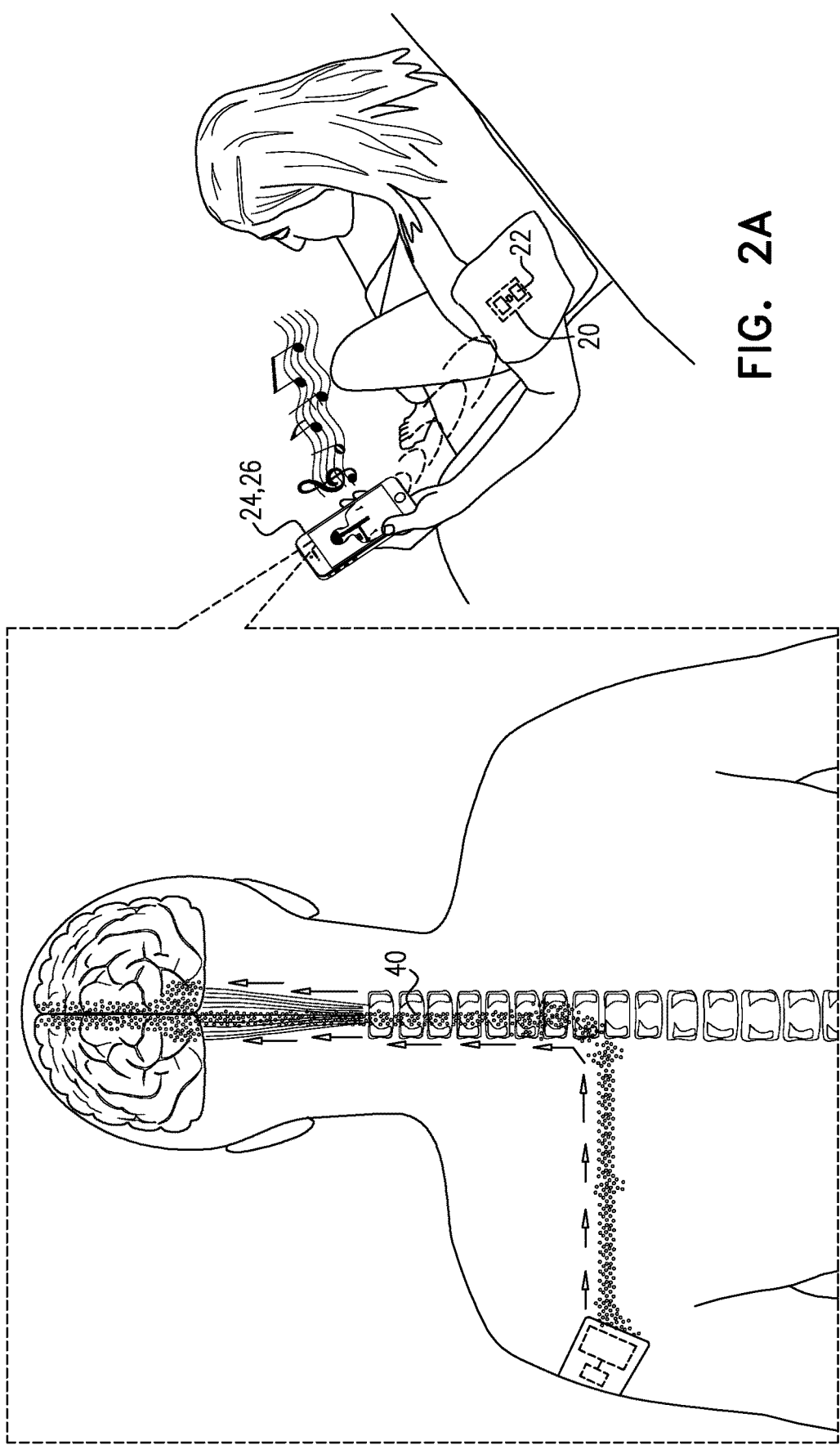
Figure 2B:
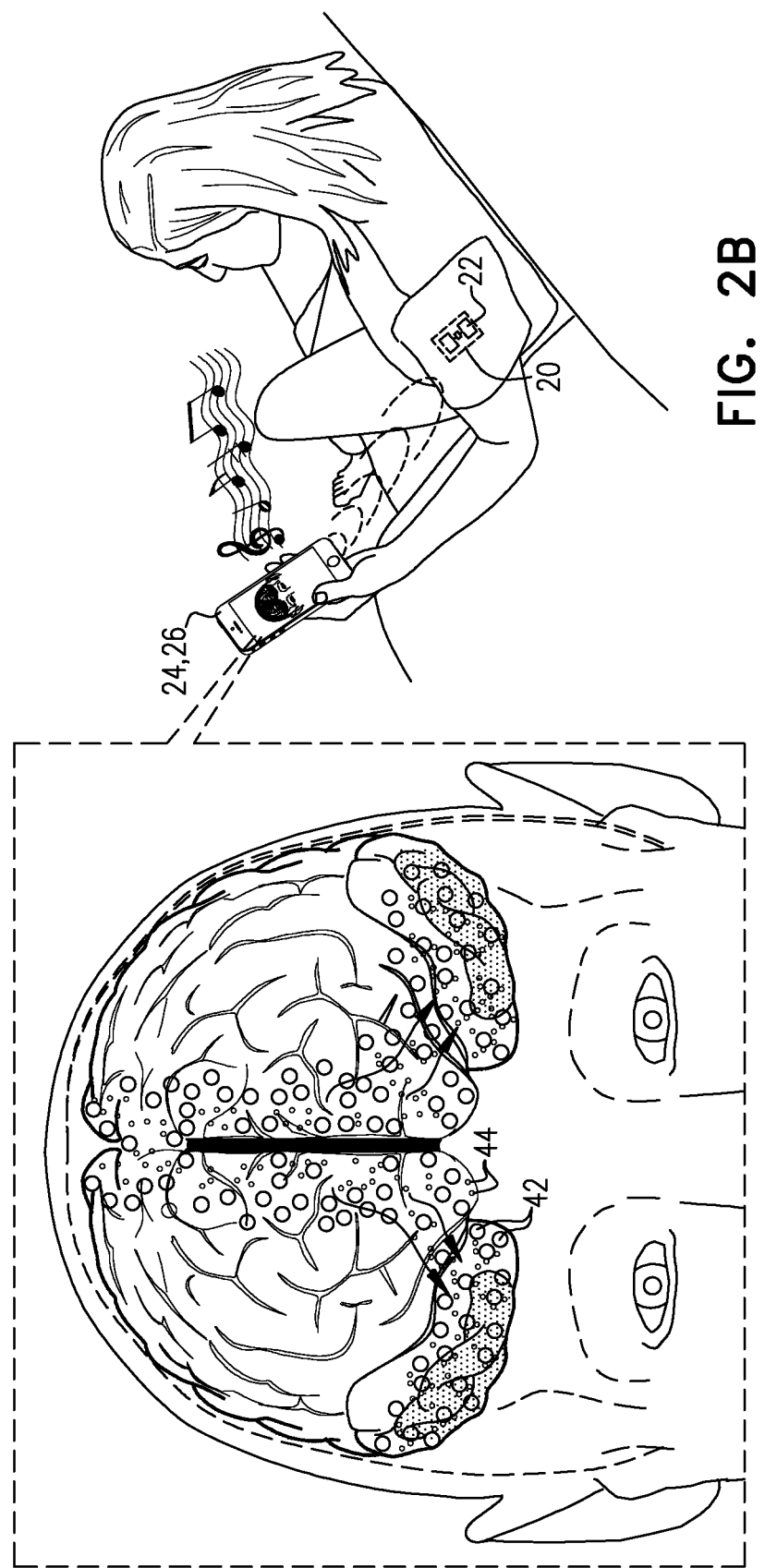
Figure 3A:
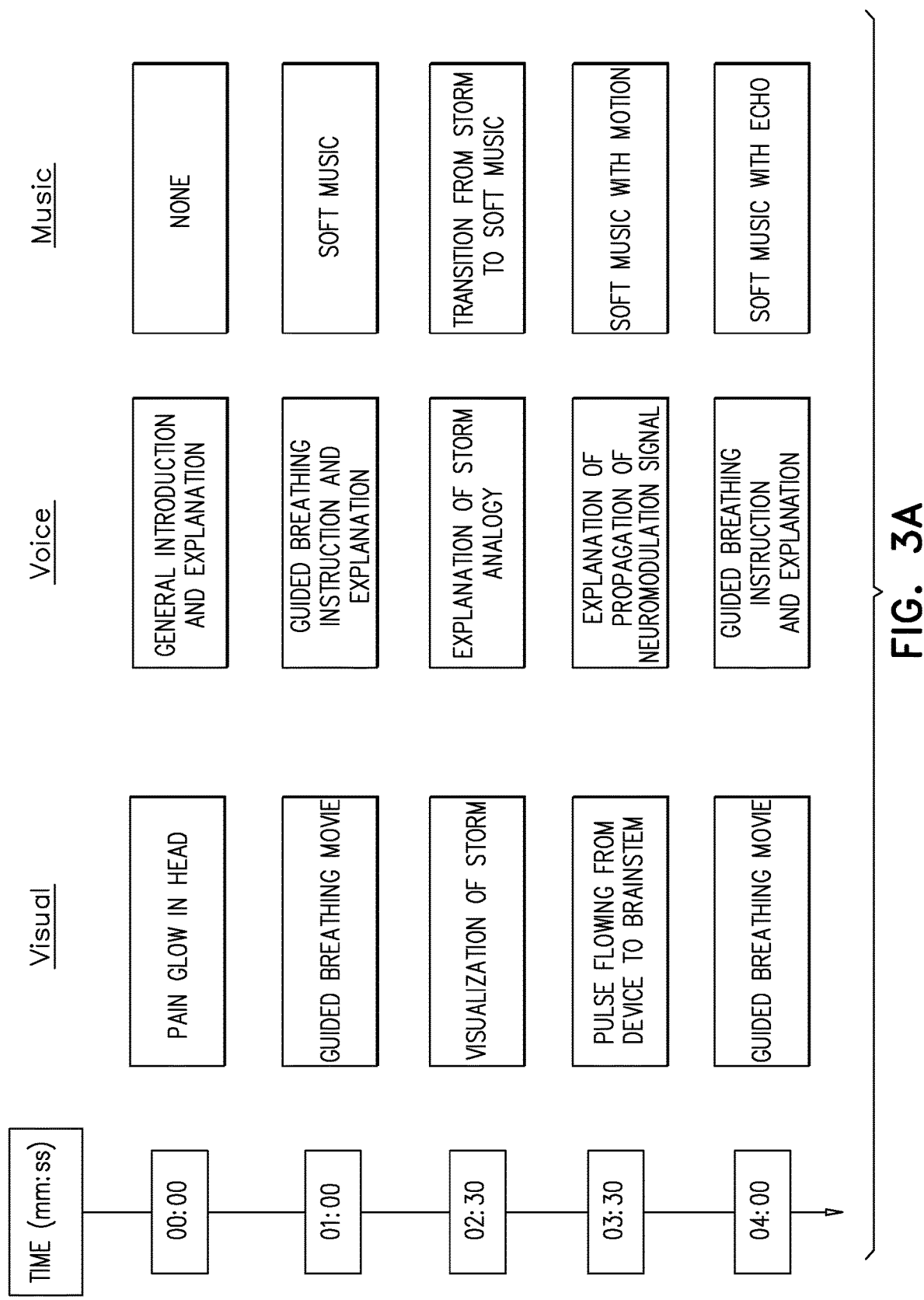
FIGS. 3A, 3B, 3C, 3D, and 3E show a timeline that provides an example of outputs that are generated to correspond with the current stage of a neuromodulation treatment and the corresponding physiological effect on the subject's body, in accordance with some applications of the present invention.
Figure 3B:
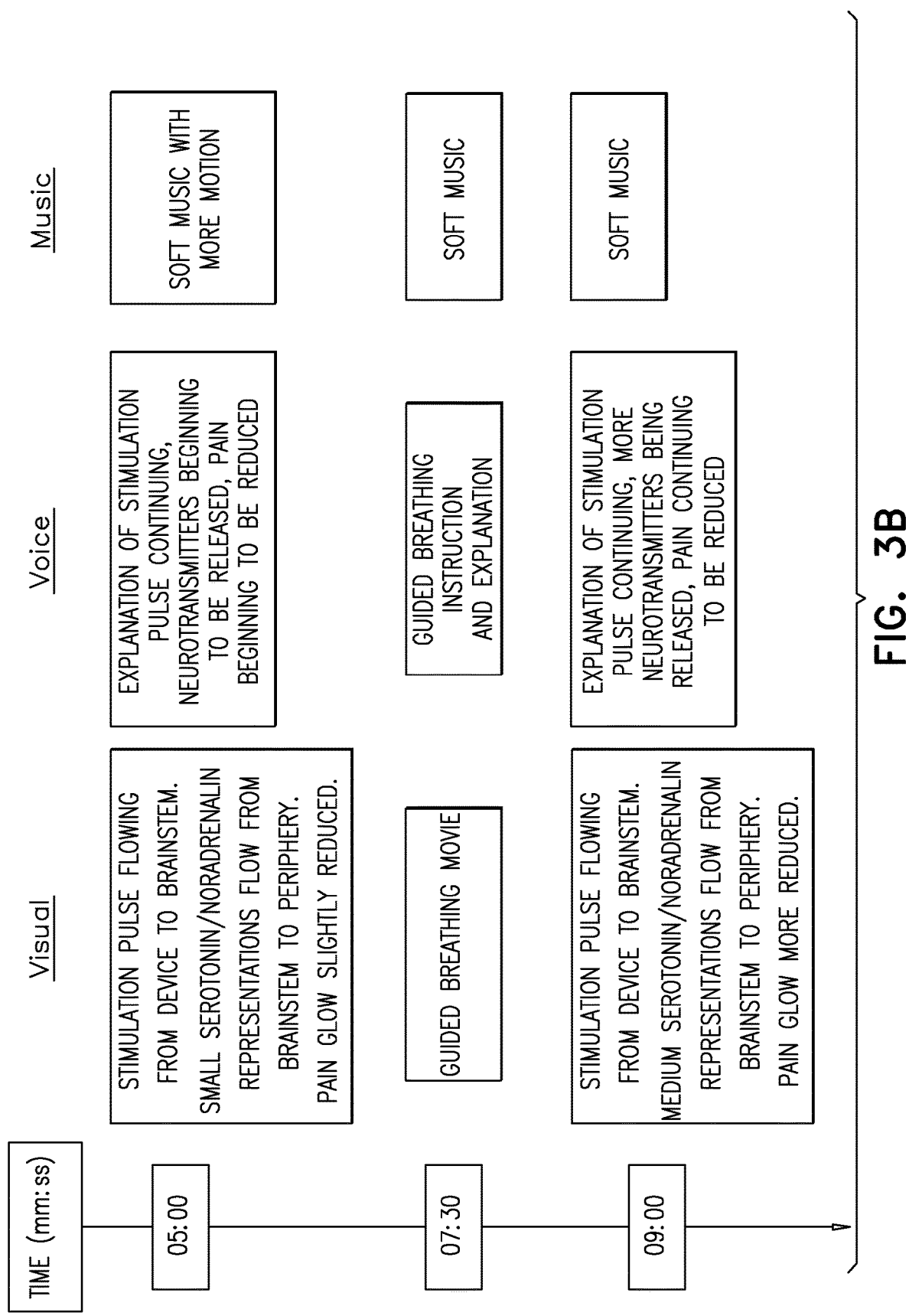
Figure 3C:
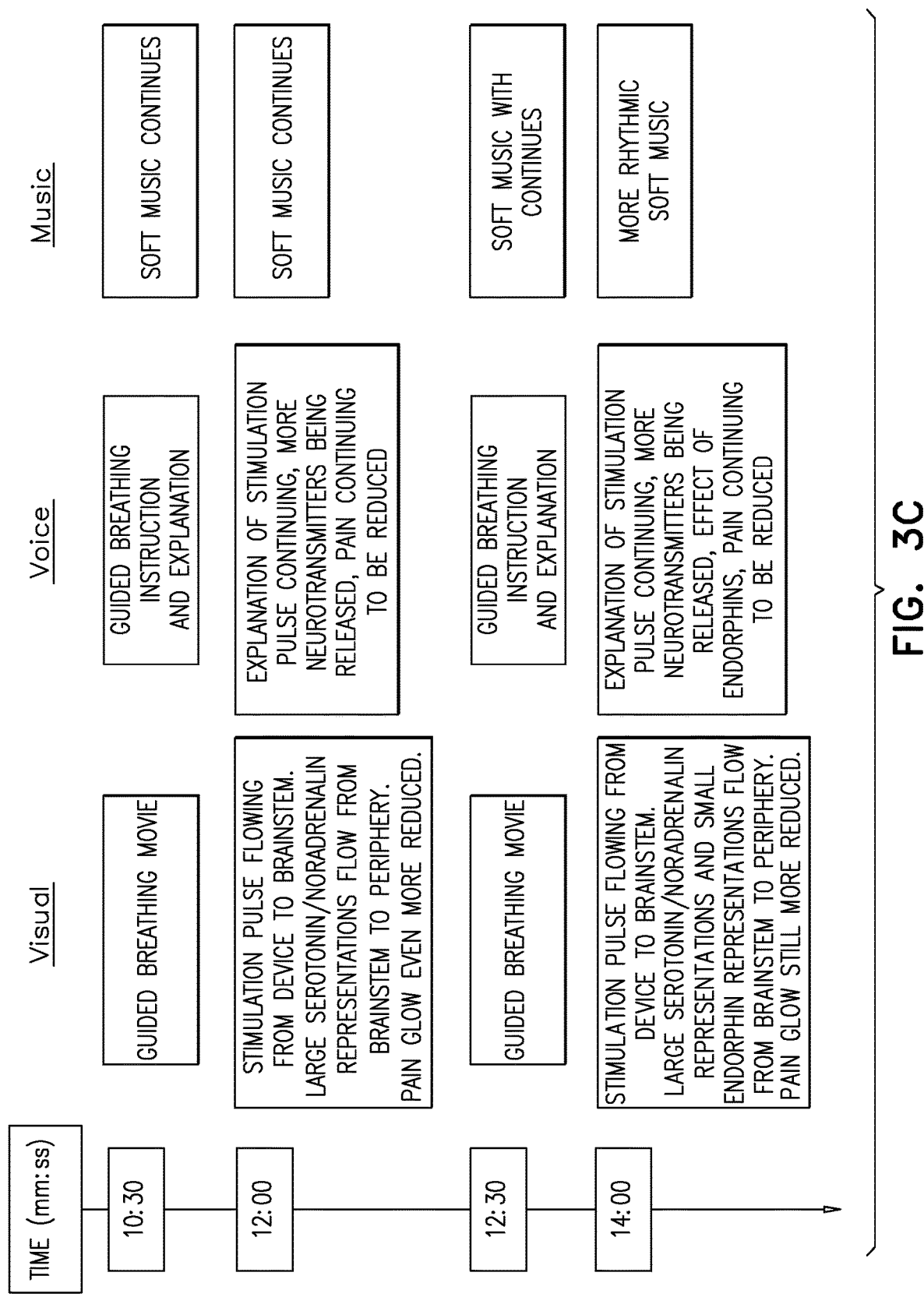
Figure 3D:
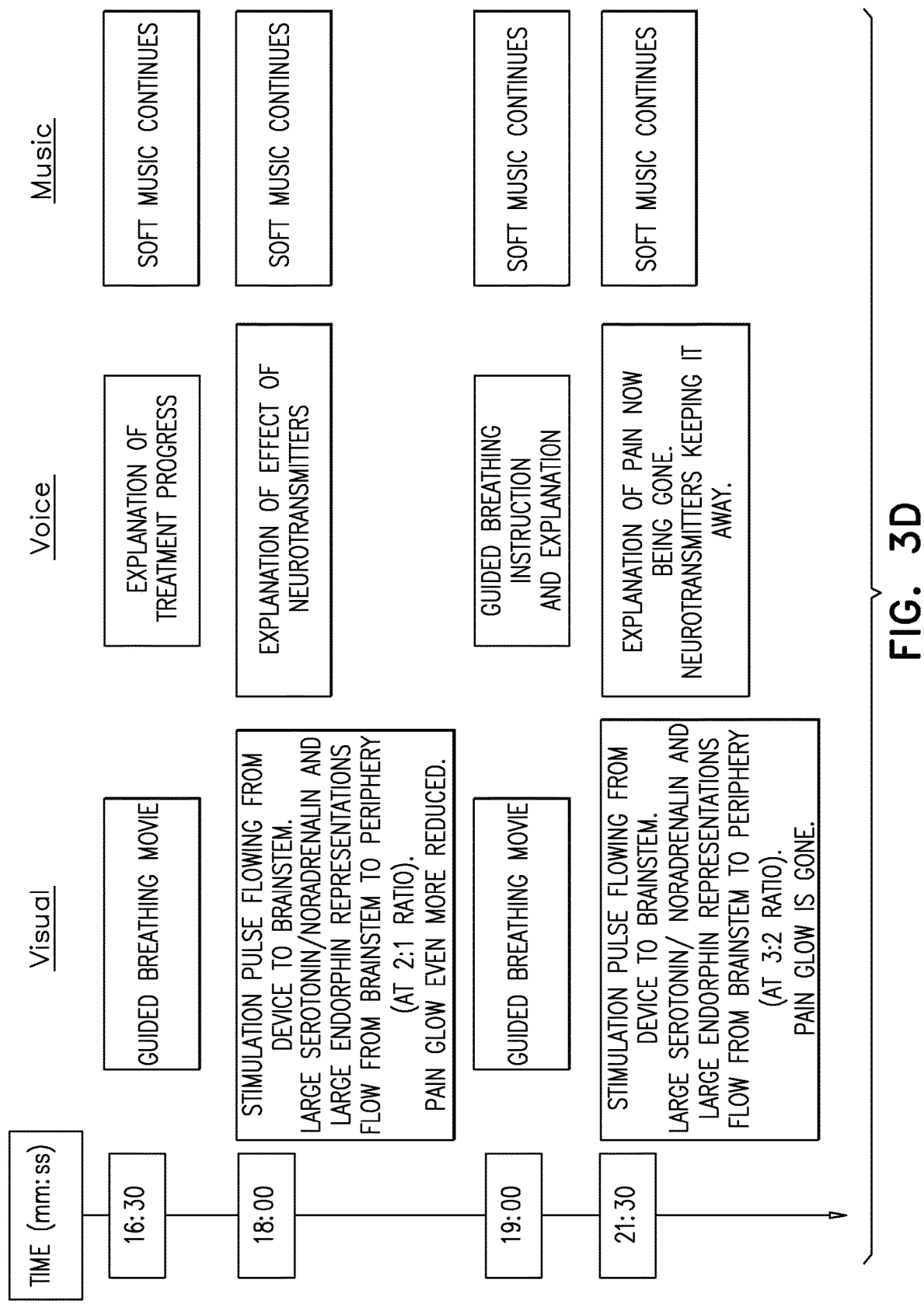
Figure 3E:
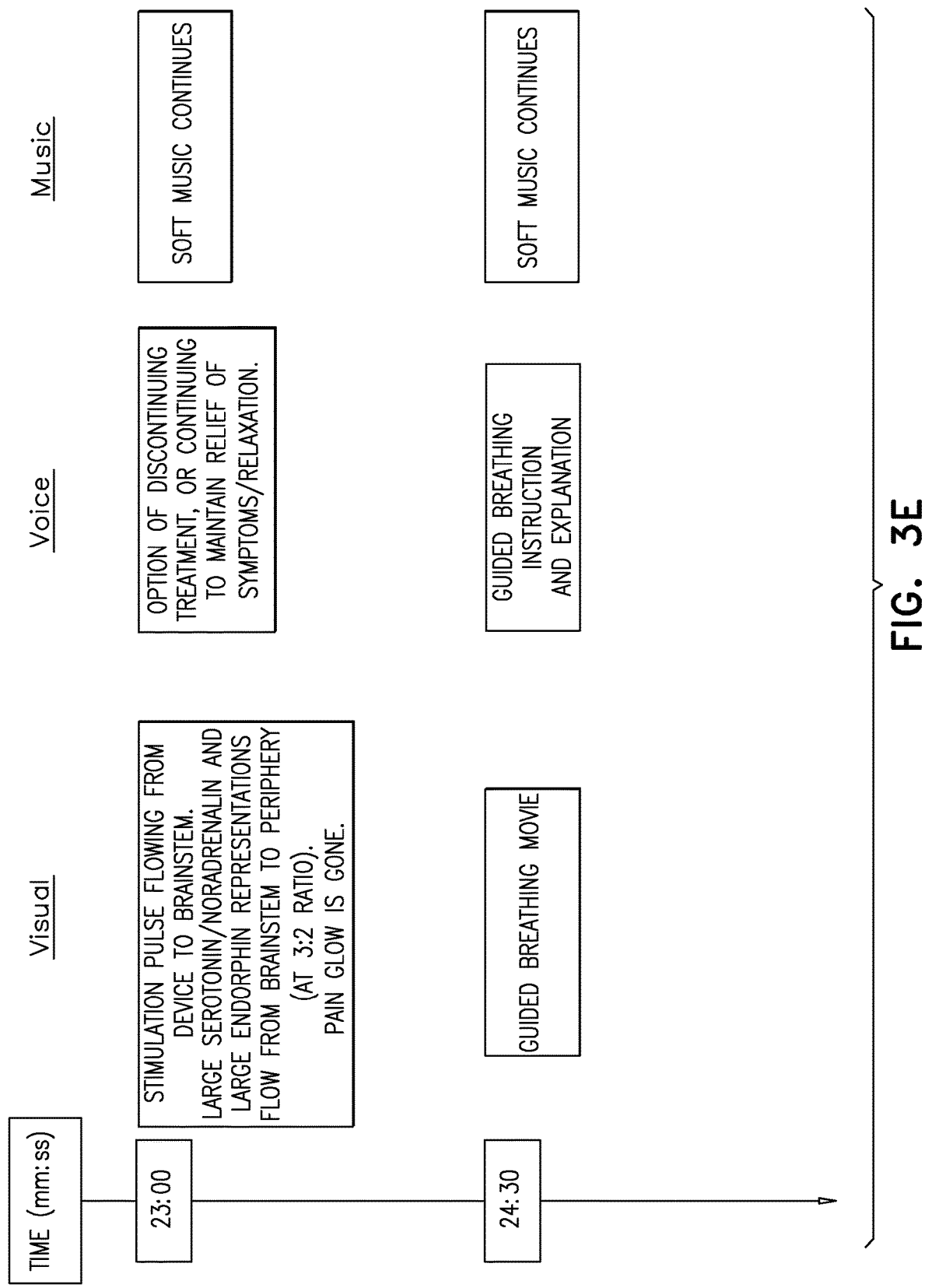

Reference is now made to FIGS. 2A, 2B, and 2C, which are schematic illustrations of examples of outputs that are generated to correspond with the current stage of a neuromodulation treatment and the corresponding physiological effect on the subject's body, in accordance with some applications of the present invention. Typically, the output is generated on user interface 26, which, as described hereinabove, may include smartphone 30, tablet device 32, and/or personal computer 34. In accordance with respective applications, the output may include an audio output, a graphical output, and/or a combined audio and graphical output (e.g., an output in movie format).

As shown in FIG. 2A, for some applications, the output includes an indication of an afferent signal propagating from the portion of the subject's body at which the electrical pulses are applied toward the central nervous system (e.g., toward the brain). For example, the output may include graphical representations of afferent neurotransmitters 40 travelling from the portion of the subject's body at which the electrical pulses are applied (the upper arm, in the example shown), toward the central nervous system (e.g., toward the brain). Alternatively or additionally, as shown in FIG. 2B, the output includes an indication of an efferent signal propagating from the central nervous system (e.g., from the brain) to a location at which the subject is feeling pain. For example, the output may include graphical representations of efferent neurotransmitters 42, 44 travelling from the central nervous system (e.g., from the brainstem) to a location at which the subject is feeling pain (e.g., the periphery of the brain, in cases in which the subject is experiencing a migraine). For some applications, respective categories of neurotransmitters are represented by respective, different graphical representations, e.g., as described in further detail hereinbelow. For example, FIG. 2B shows Serotonin/Noradrenalin graphical representations 42, as well as Endorphin graphical representations 44.

For some applications, the computer processor initially generates an output indicative of a region at which the subject feels pain prior to the neuromodulation treatment commencing. For example, as shown in FIG. 2C, if the subject is suffering from a migraine, the computer processor may drive the user interface to display an image of a head with a glow 46 within the head at a region at which the subject is feeling the migraine. For some applications, the indication of the region at which the subject is experiencing pain is generated interactively, by receiving inputs from the subject that are indicative of the type and/or location of pain that the subject is experiencing. Typically, over the duration of the neuromodulation treatment, the computer processor generates an output indicating that the size of the region and/or the level of pain is decreasing.

For some applications, the computer processor is additionally configured to generate an output (e.g., an audio output, a graphical output, and/or a combination thereof) that is configured to guide the subject through a guided relaxation procedure, and/or through a guided breathing procedure.

For some applications, one or more of the following elements is incorporated into an output that is generated in conjunction with a neuromodulation treatment of pain, in accordance with the above-described techniques:

Pain glow 46 (e.g., as shown in FIG. 2C)—For some applications, a glow is graphically depicted within an image of a head, symbolizing the sensation of headache in the brain. For example, the glow may be centered in the brainstem, and shown to radiate to the left, right, and/or center of the head. Typically, the size and color of the glow is reduced over the course of treatment, for example, from large and red, through medium-size and orange, through to small and pink, until it vanishes. For some applications, the position of the glow within the head depends on how the subject answers questions regarding the location of her/his headache, e.g., left, right, or both sides. For some applications, a pain glow is depicted at a different location within the body, for example, based upon an input from the subject indicating that he/she is feeling pain at the location.

Serotonin/Noradrenalin graphical representation 42 (e.g., as shown in FIG. 2B)—For some applications, balls or dots (or a different shape) are graphically depicted symbolizing the release of the neurotransmitters Serotonin and Noradrenalin, which act as pain killers. The size of the balls or dots may change over the course of treatment, e.g., from small, to medium, to large. Typically, these neurotransmitters are depicted as moving from the brainstem outward, and as flowing in a steady stream.

Endorphin graphical representation 44 (e.g., as shown in FIG. 2B)—For some applications, balls or dots (or a different shape) are graphically depicted symbolizing the release of the neurotransmitter Endorphin, which is related to an overall feeling of happiness. Typically, these neurotransmitters are depicted as moving from the brainstem outward, and as flowing in a stream. Further typically, the size of the graphical representation of Endorphin remains constant over the duration of the treatment, but the frequency and/or density of the graphical representation, within the stream of neurotransmitters depicted as flowing from the brain, increases over the duration of the treatment.

Electrical stimulation pulses graphical representation 40 (e.g., as shown in FIG. 2A)—For some applications, balls or dots (or a different shape) are graphically depicted symbolizing electrical stimulation pulses originating from the neuromodulation location and propagating through the nerves (e.g., the upper arm nerves), through the skeleton, and to the brainstem. For some applications, there are different sized stimulation pulse graphical representations, depending on the treatment intensity selected by the user, e.g., in accordance with the following parameters:

Very small size: intensity lower than 20 percent (of maximum intensity).
Small size: intensity between 20 and 25 percent.
Medium size: intensity between 26 and 35 percent.
Large size: intensity larger than 35 percent.

Reference is now made to FIGS. 3A, 3B, 3C, 3D, and 3E, which show a timeline that indicates an example of outputs that are generated to correspond with the current stage of a neuromodulation treatment and the corresponding physiological effect on the subject's body, in accordance with some applications of the present invention. By way of illustration and not limitation, the timeline indicates an example of an implementation of the above-described techniques, which is applied to a subject suffering from a migraine, in accordance with some applications of the present invention. For some applications, an output is generated that includes a visual component an audio (e.g., a voice) component, and/or a musical component. For some applications, in the audio output, neurotransmitters are described (for visualization purposes) as having a given appearance. Typically, for such applications, the corresponding graphical representations of the neurotransmitters in the visual output have the described appearance. In addition, for some applications the output includes an analogy for representing how the subject feels before, during and after treatment (e.g., a "storm" analogy, as described hereinbelow). For example, the timeline depicted in FIGS. 3A-E may proceed in accordance with the following table:

| Elapsed time [mm:ss] | Visual | Voice | Background music |
|---|---|---|---|
| 00:00 | A person is depicted semi-reclined in an armchair, with the device on her arm, and her smartphone in hand. Zoom on person's head. Pain glow is visible inside the head. | This audiovisual is meant to accompany you during the treatment, explain what happens during each phase of the treatment, and help you obtain the maximum relief of your migraine symptoms. Get comfortable on chair, or armchair, or even lying down on bed. Make sure the device is properly positioned on your arm. Tune the intensity of the treatment such that the stimulation on your arm is well perceived but not really painful. During the treatment, you may sometimes feel weakness or some mild twitching in the arm where the device is positioned. This is normal, not dangerous at all, and goes away as soon as the treatment is over. | No background music |
| 01:00 | Guided breathing movie. | Bring your awareness to your breath. Notice each breath as it moves into the body, and as it moves out of the body. Inhale and exhale easily, with no effort. | Soft music - no drums, no high tones, no trumpet. |

-continued

| Elapsed time [mm:ss] | Visual | Voice | Background music |
|---|---|---|---|
| | | Relax your face. Relax your forehead, the muscles between your eyebrows, relax your cheeks, your jaw, relax the neck. Let the air move easily in and out of your body. Breathe deeply, inhale slowly and fully... and then exhale slowly. Feel your stomach rising and falling slowly with each breath. Don't try to breath in any special way - just allow the body to "be breathed", naturally. | |
| 02:30 | Visualization of a storm - clouds, lightning, rain, etc. | While you are breathing deeply and easily, remember that migraine is simply a change in the electrical balance in the brain. You may imagine your migraine as a storm going on in your brain. Instead of thunder and lightning and wind and rain, it is made of electrical signals flowing your brain and running out to the nerves around your head, in your face, around the eyes, and maybe even down your neck. The treatment will help you put down the storm. | Sounds of storm (thunder, wind, rain) Back to soft music |
| 03:30 | Zoom into the person's head. Stimulation pulse graphical representation shown as flowing from device to the brainstem. | The device has already started working. It is sending special electrical signals up your arm, through your spinal cord, to your brainstem - the part in the lower center of your brain. Your brainstem is processing these signals now. The signals keep coming in, and are being processed. | A different soft music, now with some light motion. |
| 04:00 | Guided breathing movie. | Continue to breathe deeply, inhale slowly and fully... and then exhale slowly. Feel your stomach rise and fall slowly with each breath. | Soft music, with distinctive echo. |
| 05:00 | Stimulation pulse graphical representation shown as continuing to flow from device to the brainstem. Serotonin/Noradrenalin graphical representations start flowing from brainstem towards the periphery of the head. They are small. Pain glow is slightly reduced. | As your brainstem processes the signals coming from the device, it starts responding to them. It unleashes a very powerful resource that you have, a natural analgesic mechanism of your brainstem. Your brain starts releasing little chemical messengers—neurotransmitters. These specific neurotransmitters are Serotonin, and Noradrenalin. They are known to act as analgesic components, that is, natural pain killers. Imagine them as soft green balls. They start traveling down your neural system. Their role is to put the pain down. It is going to take them some time, but they are known to be effective. They travel to the receptors around your head, with one mission: to put the pain down. | Different soft music, with more motion. |

-continued

| Elapsed time [mm:ss] | Visual | Voice | Background music |
|---|---|---|---|
| 07:30 | Guided breathing movie. | Continue to breathe deeply and slowly. In and out. The pain is still there, but it may already start declining, slowly but surely.<br>In spite of the storm in your brain, you remain calm and relaxed. Let these little neurotransmitters do their thing. | Soft music |
| 09:00 | Stimulation pulse graphical representation shown as continuing to flow from device to the brainstem.<br>Serotonin/Noradrenalin graphical representation shown as continuing to flow from brainstem towards the periphery of the head. They are medium size.<br>Pain glow is reduced even more. | As more and more neurotransmitters keep traveling from your brainstem to your painful spots, the pain starts to give away.<br>It is still there, but reduced. | Soft music |
| 10:30 | Guided breathing movie. | Continue to relax your face muscles, your forehead muscles, your eyebrows muscles, your jaws.<br>Breathe deeply, in... and out. | Soft music |
| 12:00 | Zoom on the person's head.<br>Stimulation pulse graphical representation shown as continuing to flow from device to the brainstem.<br>Serotonin/Noradrenalin graphical representation shown as continuing to flow from brainstem towards the periphery of the head. They are large. | Now your brainstem is fully dedicated to fighting the pain. It sends many neurotransmitters, more and more of them, all the way to all your painful spots.<br>The pain is further reduced. | Soft music |
| 12:30 | Guided breathing movie. | Continue to relax your face muscles, your forehead muscles, your eyebrows muscles, your jaws.<br>Breathe deeply, in... and out. Let those neurotransmitters do their job, while you relax. | Soft music |
| 14:00 | Zoom into the person's head.<br>Stimulation pulse graphical representation shown as continuing to flow from device to the brainstem.<br>Serotonin/Noradrenalin graphical representation shown as continuing to flow from brainstem towards the periphery of the head. They are large.<br>Endorphin graphical representation shown as flowing from brainstem towards the periphery of the head - along with the Serotonin/Noradrenalin graphical representation. | The device keeps sending signals to your brainstem. Your brainstem continues responding by releasing analgesic neurotransmitters throughout your head, and the rest of the body.<br>As more and more electrical signals keep coming from the device, your brainstem starts releasing another type of neurotransmitters.<br>Imagine them as soft emerald balls. They travel together with the green balls, from your brainstem to the painful spots. These new neurotransmitters are called endorphins. They make you even more relaxed, less worried. | Different soft music, a little more rhythmic. |

-continued

| Elapsed time [mm:ss] | Visual | Voice | Background music |
|---|---|---|---|
| | The endorphin graphical representation is smaller than the Serotonin/Noradrenalin graphical representation. Pain glow is reduced even more. | | |
| 16:30 | Guided breathing movie. | The treatment is progressing very well. Keep breathing in... and out. Slowly. While you are relaxing, the analgesic neurotransmitters continue their relieving action. | Soft music continues. |
| 18:00 | Zoom on the person's head. Stimulation pulse graphical representation shown as continuing to flow from device to the brainstem. Serotonin/Noradrenalin and Endorphin graphical representations shown as continuing to flow from brainstem towards the periphery of the head. The Serotonin/Noradrenalin graphical representation and Endorphin graphical representation are equal in size. There are about two of the Serotonin/Noradrenalin graphical representations for every Endorphin graphical representation. Pain glow is reduced even more. | As more and more green and emerald neurotransmitters travel from your brainstem to your head and face and neck, your pain may be even further diminishing by now. | Soft music continues. |
| 19:00 | Guided breathing movie. | The treatment is very effective now. Continue to breath in... and out. Deep breaths, from your stomach. Keep breathing in... and out. Easily. This is helping your central nerve system relief of the pain. | Soft music continues. |
| 21:30 | Zoom on the person's head. Stimulation pulse graphical representation shown as continuing to flow from device to the brainstem. Serotonin/Noradrenalin and Endorphin graphical representations shown as continuing to flow from brainstem towards the periphery of the head. They are equal in size. There are about three of the Serotonin/Noradrenalin graphical representations for every two of the Endorphin graphical representations. Pain glow is gone. | The storm in your brain is over now. By now, your pain might have almost gone away, or even completely gone away. The device keeps sending those electrical signals, and as a result your brainstem continues releasing analgesic neurotransmitters, just to make sure the pain does not come back. | Soft music continues. |
| 23:00 | Zoom on the person's head. Stimulation pulse graphical representation shown as continuing to | You may stop the treatment soon if your pain has completely gone away, or you may let it continue for some more time, while you breathe | Soft music continues. |

-continued

| Elapsed time [mm:ss] | Visual | Voice | Background music |
|---|---|---|---|
| | flow from device to the brainstem. Serotonin/Noradrenalin and Endorphin graphical representations shown as continuing to flow from brainstem towards the periphery of the head. They are equal in size. There are about three of the Serotonin/Noradrenalin graphical representations for every two of the Endorphin graphical representations. Pain glow is gone. | deeply and slowly. | |
| 24:30 | Guided breathing movie. | Remain calm, and breathe deeply and easily throughout the remaining duration of the treatment. | Soft music continues. |

Figure 4:
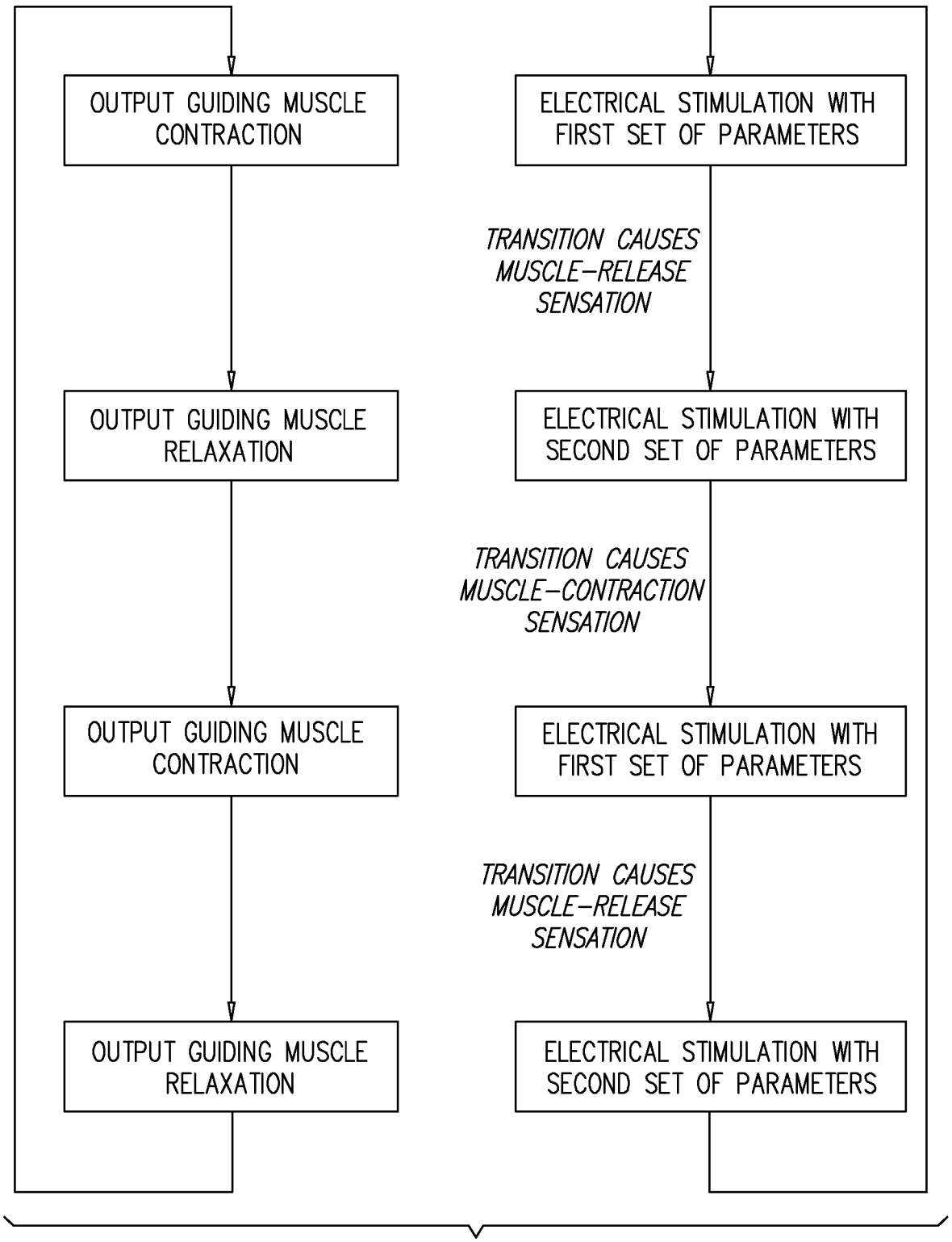
FIG. 4 is a flowchart showing steps of a muscle-relaxation method that is performed, in accordance with some applications of the present invention.

Reference is now made to FIG. 4, which is a flowchart showing steps of a muscle-relaxation method that is performed, in accordance with some applications of the present invention. The left and right portions of the flowchart shown in FIG. 4 are typically performed simultaneously with each other, with each of the boxes in the left portion being performed at the same time as the respective, corresponding box in the right portion of the flowchart. For some applications, relaxation techniques are used to contain feelings of anxiety, which commonly contribute to the development of migraine, and/or other forms of pain (e.g., as described hereinabove). For some applications, a subject is guided to relax his/her muscles by providing a muscle-relaxation neuromodulation treatment, in combination with muscle-relaxation guidance.

For example, as shown in FIG. 4, an output may be generated such as to guide the subject to contract a muscle during a first time period, and to release tension in the muscle during a second time period, the first and second periods being applied in an alternating cycle. At the same time, an electrical stimulation signal may be applied to a portion of the subject's body that is configured to contract a muscle of the subject during the first time period, and to release tension in the muscle, during the second time period. Thus, typically, due to the electrical stimulation (a) in transitions from the second period to the first period, the subject senses a contraction sensation, and (b) in transitions from the first period to the second period, the subject senses a tension-release sensation. In this manner, the guidance and the electrical stimulation typically have a synergistic effect, and enhance muscle relaxation. For example, the electrical stimulation signal may be applied at a first pulse width during the first period (e.g., a pulse width of between 160 and 240 microseconds (e.g., between 180 and 220 microseconds, e.g., approximately 200 microseconds)), and at a second pulse width (e.g., a pulse width of between 60 and 140 microseconds (e.g., between 80 and 120 microseconds, e.g., approximately 100 microseconds)) during the second period, in synchronization with the generated output, such that, due to the electrical stimulation (a) in transitions from the second period to the first period, the subject senses a contraction sensation, and (b) in transitions from the first period to the second period, the subject senses a tension-release sensation.

For some applications, the first time period (during which the output guides the user to contract his/her muscle) is shorter than the second time period (during which the output guides the user to release tension in his/her muscle). For example, a ratio between the first time period and the second time period may be between 2:3 and 1:3, e.g., approximately 1:2. For example, the first time period may be 10 seconds and the second time period may be 20 seconds.

For some applications, the output configured to guide the subject to contract the muscle during the first time period, and to release tension in the muscle during the second time period is generated on user interface 26, which, as described hereinabove, may include smartphone 30, tablet device 32, and/or personal computer 34. In accordance with respective applications, the output may include an audio output, a graphical output, and/or a combined audio and graphical output (e.g., an output in movie format).

For some applications, the technique described with reference to FIG. 4 is combined with the pain-relief neuromodulation techniques described hereinabove. For some applications, the electrical stimulation pulses that are applied via electrodes 22 of patch 20 (and that are used for a pain-relief neuromodulation treatment as described hereinabove) are modulated to enhance an accompanying relaxation session, by creating a physical sensation of a contraction-release cycle. Typically, this is performed by modulating the pulse width of the electrical stimulation pulses, such that during first and second periods of the electrostimulation, which alternate with each other, the electrical stimulation is applied using respective pulse widths. For example, a first pulse width of between 160 and 240 microseconds (e.g., between 180 and 220 microseconds, e.g., approximately 200 microseconds) may be used for the first time period. Subsequently, a second pulse width of between 60 and 140 microseconds (e.g., between 80 and 120 microseconds, e.g., approximately 100 microseconds) may be used for the second time period. As described hereinabove, the first and second time periods are typically applied in an alternating cycle. The transition from the first pulse width to the second pulse width typically generates a tension-release sensation in the subject, while the transition from the second pulse width to the first pulse width typically generates a contraction sensation in the subject. Typically, both the pulse widths that are used are effective for providing the pain-relief therapy. Further typically, the cycle of the electrical stimulation periods is synchronized with the output that is generated by the computer processor for guiding the subject to perform cycles of muscle contraction, followed by release, as described hereinabove. In this manner, there is typically synergy between the guided exercises and the cycles of stimulation that are applied to the subject.

For some applications, the electrical stimulation signal described with reference to FIG. 4 is applied to the subject via a different set of electrodes from electrodes 22. For example, the electrical stimulation signal that is configured to relax the subject's muscles may be applied to muscles of the subject's shoulders via electrodes 50 on patch 52, shown in FIG. 1. Alternatively or additionally, the electrical stimulation signal that is configured to relax the subject's muscles may be applied to other muscles, e.g., muscles of the face, the forearm, the hand, the legs, the feet, etc., mutatis mutandis. For some applications, the electrical stimulation signal that is configured to relax the subject's muscles and the corresponding output that is configured to guide the subject to relax his/her muscles is applied at the same time as a pain-relief neuromodulation treatment (e.g., as described hereinabove) is applied via electrodes 22 of patch 20. For some applications, the electrical stimulation signal that is configured to relax the subject's muscles and the corresponding output that is configured to guide the subject to relax his/her muscles is applied in the absence of a pain-relief neuromodulation treatment (e.g., as described hereinabove) being applied via electrodes 22 of patch 20.

For some applications, the computer processor is configured to drive the electrodes to provide stimulation to the subject to prevent the onset of headaches, migraines, fibromyalgia, dysmenorrhea, post-traumatic headache, and/or another form of pain, before such events are sensed by the subject. For example, a pain-relief neuromodulation treatment and/or a muscle-relaxation treatment as described herein may be delivered at regular intervals, e.g., daily. In accordance with respective applications, the computer processor (via a program or application running on the processor) may facilitate the scheduling of such treatments, and/or may automatically alert the subject when necessary, in order to facilitate compliance with the treatment schedule.

For some applications, the above-described pain-relief neuromodulation treatment and/or a muscle-relaxation treatment is used to provide electrical stimulation to a subject suffering from a condition other than a migraine, a headache, fibromyalgia, dysmenorrhea, or pain. Furthermore, the scope of the present application includes applying electrical stimulation signals to a subject having signal characteristics as described herein, but via a different type of electrodes to those described hereinabove. For example, the stimulation may be applied via implanted electrodes, subcutaneous electrodes, and/or any other type of electrodes configured to electrically stimulate a subject.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 24. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semi-conductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 24) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 24) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 24 and the other computer processors described herein are typically hardware devices programmed with computer program instructions to produce a special purpose computer. For example, when programmed to perform the methods described herein, the computer processor typically acts as a special purpose electrical-stimulation computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   electrodes configured to be placed upon a portion of a body of a subject;
   a user interface device; and
   at least one computer processor configured to:
     apply a neuromodulation treatment to the subject, by driving electrical pulses into the portion of the subject's body via the electrodes,
     generate an output on the user interface device that indicates to the subject a physiological effect that the neuromodulation treatment has upon the subject's body,
   the output indicative of an afferent signal propagating from the portion of the subject's body toward a central nervous system of the subject.

2. The apparatus according to claim 1, wherein the computer processor is configured to reduce pain in a location of the subject's body that is at a distance of more than 25 cm from the portion of the subject's body into which the electrical pulses are driven, by driving the electrical pulses into the portion of the subject's body.

3. The apparatus according to claim 1, wherein the at least one computer processor is configured to reinforce an effectiveness of the neuromodulation treatment, by generating the output.

4. The apparatus according to claim 1, wherein the at least one computer processor is configured to generate the output by generating an audio output.

5. The apparatus according to claim 1, wherein the at least one computer processor is configured to generate the output by generating a combined audio and graphical output.

6. Apparatus comprising:
   electrodes configured to be placed upon a portion of a body of a subject;
   a user interface device; and
   at least one computer processor configured to:
     apply a neuromodulation treatment to the subject, by driving electrical pulses into the portion of the subject's body via the electrodes,
     generate an output on the user interface device that indicates to the subject a physiological effect that the neuromodulation treatment has upon the subject's body,
   the output indicative of an efferent signal propagating from a central nervous system of the subject to a location at which a subject is feeling pain.

7. Apparatus comprising:
   electrodes configured to be placed upon a portion of a body of a subject;
   a user interface device; and
   at least one computer processor configured to:
     apply a neuromodulation treatment to the subject, by driving electrical pulses into the portion of the subject's body via the electrodes,
     generate an output on the user interface device that indicates to the subject a physiological effect that the neuromodulation treatment has upon the subject's body,
   the output indicative of a region at which the subject feels pain prior to the neuromodulation treatment commencing, and indicating that a size of the region decreases over a duration of the neuromodulation treatment.

8. Apparatus comprising:
   electrodes configured to be placed upon a portion of a body of a subject;
   a user interface device; and
   at least one computer processor configured to:
     apply a neuromodulation treatment to the subject, by driving electrical pulses into the portion of the subject's body via the electrodes,
     generate an output on the user interface device that indicates to the subject a physiological effect that the neuromodulation treatment has upon the subject's body, and
     generate an output that is configured to guide the subject through a guided relaxation procedure.

9. Apparatus comprising:
   electrodes configured to be placed upon a portion of a body of a subject;
   a user interface device; and
   at least one computer processor configured to:
     apply a neuromodulation treatment to the subject, by driving electrical pulses into the portion of the subject's body via the electrodes,
     generate an output on the user interface device that indicates to the subject a physiological effect that the neuromodulation treatment has upon the subject's body, and
     generate an output that is configured to guide the subject through a guided breathing procedure.

10. The apparatus according to claim 1, wherein the at least one computer processor is configured to generate the output by generating a graphical output in which respective categories of neurotransmitters are represented by respective, different graphical representations.

11. A method comprising:
    applying a neuromodulation treatment to a subject, by driving electrical pulses into a portion of a body of the subject; and
    generating an output that indicates to the subject a physiological effect that the neuromodulation treatment has upon the subject's body, the output indicative of an afferent signal propagating from the portion of the subject's body toward a central nervous system of the subject.

12. The method according to claim 11, wherein driving electrical pulses into the portion of the subject's body comprises reducing pain in a location of the subject's body that is at a distance of more than 25 cm from the portion of the subject's body into which the electrical pulses are driven.

13. The method according to claim 11, wherein generating the output comprises reinforcing an effectiveness of the neuromodulation treatment, by generating the output.

14. The method according to claim 11, wherein generating the output comprises generating an audio output.

15. The method according to claim 11, wherein generating the output comprises generating a combined audio and graphical output.

16. A method comprising:
applying a neuromodulation treatment to a subject, by driving electrical pulses into a portion of a body of the subject, and
generating an output that indicates to the subject a physiological effect that the neuromodulation treatment has upon the subject's body, the output indicative of an efferent signal propagating from a central nervous system of the subject to a location at which a subject is feeling pain.

17. A method comprising:
applying a neuromodulation treatment to a subject, by driving electrical pulses into a portion of a body of the subject; and
generating an output that indicates to the subject a physiological effect that the neuromodulation treatment has upon the subject's body, the output indicative of a region at which the subject feels pain prior to the neuromodulation treatment commencing, and indicating that a size of the region decreases over a duration of the neuromodulation treatment.

18. A method comprising:
applying a neuromodulation treatment to a subject, by driving electrical pulses into a portion of a body of the subject;
generating an output that indicates to the subject a physiological effect that the neuromodulation treatment has upon the subject's body; and
generating an output that is configured to guide the subject through a guided relaxation procedure.

19. A method comprising:
applying a neuromodulation treatment to a subject, by driving electrical pulses into a portion of a body of the subject;
generating an output that indicates to the subject a physiological effect that the neuromodulation treatment has upon the subject's body; and
generating an output that is configured to guide the subject through a guided breathing procedure.

20. A method comprising:
applying a neuromodulation treatment to a subject, by driving electrical pulses into a portion of a body of the subject; and
generating an output that indicates to the subject a physiological effect that the neuromodulation treatment has upon the subject's body,
wherein generating the output comprises generating a graphical output in which respective categories of neurotransmitters are represented by respective, different graphical representations.

* * * * *